US008865248B2

(12) United States Patent
Stevenson et al.

(10) Patent No.: US 8,865,248 B2
(45) Date of Patent: Oct. 21, 2014

(54) METHOD OF MANUFACTURING A MEDICAMENT DISPENSER DEVICE

(75) Inventors: Paul Stevenson, Little Weighton (GB); Darren Bromley-Davenport, Marton (GB)

(73) Assignee: Portal Medical Ltd., Chester (GB)

( * ) Notice: Subject to any disclaimer, the term of this patent is extended or adjusted under 35 U.S.C. 154(b) by 0 days.

(21) Appl. No.: 13/580,951

(22) PCT Filed: Feb. 23, 2011

(86) PCT No.: PCT/GB2011/050352
§ 371 (c)(1),
(2), (4) Date: Oct. 2, 2012

(87) PCT Pub. No.: WO2011/104541
PCT Pub. Date: Sep. 1, 2011

(65) Prior Publication Data
US 2013/0019863 A1    Jan. 24, 2013

(30) Foreign Application Priority Data

Feb. 26, 2010    (GB) .................................. 1003275.3

(51) Int. Cl.
| | | |
|---|---|---|
| *C08F 2/46* | (2006.01) | |
| *C08J 7/18* | (2006.01) | |
| *A61M 11/00* | (2006.01) | |
| *B05D 3/04* | (2006.01) | |
| *A61M 15/00* | (2006.01) | |
| *B05D 1/00* | (2006.01) | |
| *B05D 7/22* | (2006.01) | |
| *B05D 5/08* | (2006.01) | |

(52) U.S. Cl.
CPC . *B05D 1/62* (2013.01); *B05D 7/227* (2013.01); *A61M 15/009* (2013.01); *B05D 5/083* (2013.01); *A61M 2205/0238* (2013.01); *A61M 2205/0222* (2013.01)
USPC ........ 427/2.1; 427/487; 427/488; 128/200.23

(58) Field of Classification Search
None
See application file for complete search history.

(56) References Cited

U.S. PATENT DOCUMENTS

| | | |
|---|---|---|
| 8,372,491 B2 | 2/2013 | Rostaing |
| 2006/0068224 A1 | 3/2006 | Grobe et al. |

FOREIGN PATENT DOCUMENTS

| | | |
|---|---|---|
| CN | 101522224 A | 9/2009 |
| EP | 0642992 A2 | 3/1995 |
| EP | 1066073 B1 | 6/2002 |
| JP | 2006102499 A | 4/2006 |
| WO | 02060509 A1 | 8/2002 |
| WO | 02100928 A1 | 12/2002 |

(Continued)

OTHER PUBLICATIONS

ISA European Patent Office, International Search Report and Written Opinion of PCT/GB2011/050352, Jul. 21, 2011, Netherlands, 9 pages.

*Primary Examiner* — Cachet Sellman
(74) *Attorney, Agent, or Firm* — Alleman Hall McCoy Russell & Tuttle LLP

(57) ABSTRACT

According to the invention there is provided a method of treating a component of a medicament dispenser device, the component having one or more surfaces which come into contact with the medicament during storage or use of the device, the method including the steps of:
 providing said component; and
 coating at least one of said surfaces by plasma deposition thereby to inhibit surface deposition or degradation of the medicament, wherein at least part of the plasma deposition is performed under DC bias control.

20 Claims, 2 Drawing Sheets

(56) References Cited

FOREIGN PATENT DOCUMENTS

| WO | 2008146022 A2 | 12/2008 |
| WO | 2008146024 A2 | 12/2008 |
| WO | WO 2008146022 A2 * | 12/2008 |
| WO | WO 2008146025 A2 * | 12/2008 |

* cited by examiner

METHOD OF MANUFACTURING A MEDICAMENT DISPENSER DEVICE

CROSS-REFERENCE TO RELATED APPLICATIONS

The present application is the U.S. national phase of PCT/GB2011/050352, filed Feb. 23, 2011, and entitled, "Method of Manufacturing a Medicament Dispenser Device," which claims priority to GB Application No. 1003275.3, filed Feb. 26, 2010, the entire disclosures of each of which are hereby incorporated by reference in their entirety for all purposes.

It is well known to administer medicaments to a patient by inhalation using pressurised dispenser devices which dispense the medicament in a carrier fluid, commonly as an aerosol. Such devices are often referred to as pressurised metered dose inhalers (pMDIs), and are very commonly used for treating asthma and chronic obstructive pulmonary disease (COPD).

One problem associated with dispenser devices of this kind is absorption of the active medicament on the internal surfaces of the device. This in turn can lead to a loss of potency and/or erratic dosing during the shelf-life of the device. In some instances clustering of drug particles can occur if the active medicament is present as a suspension of particles. One approach that has been adopted in order to reduce the surface absorption of the active drug is to modify the surface properties of the device, and traditionally this has been done by spray-coating with a low energy polymer. However, this process can be difficult to manage, and often the quality of the surface coatings is variable.

It is known from, for example, EP0642992, EP1066073 and WO2008/146024 that various interior surfaces of pMDI devices can be provided with coatings deposited by plasma polymerisation. Plasma polymerisation is highly desirable since it is a low temperature technique. However, the present inventors have also realised that there are drawbacks associated with prior art plasma polymerisation techniques, and that, in order to provide a practical, commercial approach which is economic to utilise and results in coatings having acceptable physical and chemical properties, there is a need to develop new and improved techniques. Examples of drawbacks include non-uniform coating deposition, the length of time taken to deposit the polymerised layer, and the performance characteristics of the coating in use in a dispenser device. A further drawback is that after plasma polymerisation, the coating is typically shelved/conditioned for one to seven days to allow reorientation of reactive unsaturated sites on the surface of the plasma coating which are created as part of the plasma polymerisation process. In addition to slowing down the manufacturing process by necessitating a sizeable rest period before the product can be used, the present inventors have realised that undesirable species such as water, hydroxyl groups and species present in the atmosphere can be absorbed onto/react with the plasma coated surface (reactive sites remaining) during the rest period.

The present invention, in at least some of its embodiments, addresses the above-described problems and needs.

According to a first aspect of the invention there is provided a method of treating a component of a medicament dispenser device, the component having one or more surfaces which come into contact with the medicament during storage or use of the device, the method including the steps of:
providing said components; and
coating at least one of said surfaces by plasma deposition thereby to inhibit surface deposition or degradation of the medicament, wherein at least part of the plasma deposition is performed under DC bias control.

Preferably, the plasma deposition comprises plasma polymerising at least one monomer. Alternatively, an inorganic coating may be plasma deposited.

In this way, a very efficient plasma polymerisation process can be provided which results in a uniform coating with an optimum deposition rate.

The DC bias control may be performed using a DC bias voltage in the range of 50-800 volts, preferably in the range of 50-500 volts, most preferably in the range of 50-350 volts.

It is preferred that for metallic components the component is earthed during the step of plasma deposition, such as plasma polymerising the monomer. The present inventors have realised that if the component is instead held at RF potential, then the plasma produced can be too intense, causing coating to be removed. This is a particular problem in embodiments in which the component is a can body. Another way in which plasma polymerisation can be performed is to allow the potential of the component to float. This approach is the less preferred in embodiments in which the component is metallic, since in these embodiments charge is easily dissipated and attraction of the coating species is significantly reduced, which can lead to a weakly bound and porous coating. Components formed from insulating materials such as polymers may be allowed to float.

In embodiments in which the component is a can body, it is advantageous that during the step of plasma deposition, an RF potential is applied to an electrode which is positioned within the can body. This configuration can result in particularly uniform coatings over the entire interior surface of the can body.

Advantageously, the step of plasma deposition is performed in a substantial absence of oxygen. It has been found that the presence of oxygen has a deleterious effect on a polymerised coating, and can also have a deleterious effect on some medicaments. Advantageously, the coating produced by the plasma deposition has an oxygen content of less than 10 At %, preferably less than 5 At %, most preferably less than 2 At % as measured by X-Ray Photoelectron Spectroscopy (XPS) when the monomer or other precursor itself does not contain oxygen.

The step of plasma deposition may be initially performed without DC bias control, with DC bias control being commenced a period of time after plasma deposition begins. The step of plasma polymerising deposition may be initially performed using forward power control.

Power is supplied to the plasma during plasma polymerisation of the monomer. Advantageously, the step of plasma polymerising the monomer is completed by turning off the power supply to the plasma whilst maintaining a supply of the monomer so that the plasma diminishes by using up a capacitive reservoir of electrons, thereby providing surface quenching of the coating. In this way, after the power supply is switched off the plasma can slowly diminish, as electrons in the capacitive reservoir are allowed to discharge. This results in partially ionised plasma of reducing intensity which flushes the surface. Finally, the surface is flushed by neat, unionised monomer. Combined, this has the surprising effect of "capping off" unsaturated sites to form a stable surface prior to the component being removed from the site of the plasma polymerisation (typically a plasma chamber). This provides the significant advantage of obviating any need for a rest period before the component can be used. The supply of the monomer may be maintained for a time in the range 5 seconds to 10 minutes after the power supply to the plasma is turned off. Preferably, the supply is maintained for a time in the range of 30 to 60 seconds.

The monomer or monomers may be one or more of a hydrocarbon, fluorocarbon, silane or siloxane. A single monomer may be used, or a mixture of monomers may be utilised. Suitable per-fluorocarbon precursors include $C_nF_{2n+2}$ where n is in the range of 1 to 8, and the chemicals HFA134a (1,1,1,2,-tetrafluoroethane) and HFA227 (1,1,1,2, 3,3,3-heptafluoropropane), which are commonly used as propellants in medicament dispenser devices. Cyclic per-fluorocarbons may be used, and a particularly preferred embodiment is $C_4F_8$. Unsaturated per-fluorocarbons might be used.

In embodiments in which the precursor is a hydrocarbon, alkanes of the formula $C_nH_{2n+2}$ where n is 1 to 12 can be used. Methane and ethane are particularly preferred. $C_3H_8$, $C_4H_{10}$ and $C_5H_{12}$ are also preferred embodiments. Alkenes, alkynes and cyclic hydrocarbons may be used as the precursor.

The coating can be of any desired thickness. Typically, the thickness is in the range of 15-500 nm, with the range of 15-125 nm being preferred. However, it is possible to provide coatings of other thicknesses, and thicknesses in the range of 300-400 nm are commercially attractive.

The component may undergo a cleaning step prior to the step of plasma polymerising the monomer. Preferably, the cleaning step utilises a plasma cleaning treatment, and most preferably a plasma is formed using argon. It is important that oxygen is excluded from any cleaning step, since oxygenation of the surface of the component can make the subsequent step or steps more difficult to carry out. Additionally, any oxygen absorbed into the walls of the processing apparatus can leach out and disassociate a subsequently deposited plasma coating, making the subsequent plasma coating step more difficult and disadvantageous as well.

The surface of the component may be surface modified prior to the step of plasma polymerising the monomer, wherein the surface modification takes place in a plasma treatment step using a fluorine and/or carbon containing precursor under conditions including a substantial absence of oxygen which results in the surface substantially comprising metal-fluoride and/or metal carbide moieties after the surface modification. The surface modification step is performed prior to the step of plasma polymerising the monomer, and generally is performed after any cleaning step. Generally, a more intense plasma is utilised during the surface modification step in order to efficiently disassociate the fluorine and/or carbon containing precursor into reactive fluorine and/or carbon. The per-fluorocarbons and hydrocarbons discussed above may also be used for the surface modification step. Methane, ethane and $CF_4$, $C_2F_6$, $C_3F_8$ and $C_4F_8$ are particularly preferred. The surface modification and subsequent plasma polymerisation of the monomer may form a single continuous process. In one embodiment, a plasma is initially performed using either DC bias or forward power control in order to effect the surface modification, with DC bias control being maintained or commenced later in order to effect the step of plasma polymerising the monomer.

According to a second aspect of the invention there is provided a method of manufacturing a medicament dispenser device, the method including the steps of:
treating a component of the dispenser device in a method according to the first aspect of the invention;
providing other components of the device; and
assembling the components to provide an assembled medicament dispenser device.

According to a third aspect of the invention there is provided a dispenser device for dispensing a medicament, the device including at least one component treated in a method according to the first aspect of the invention.

The component may have a coating produced by the plasma deposition which has an oxygen content of less than 2 At % as measured by XPS.

According to a fourth aspect of the invention there is provided a dispenser device for dispensing medicament, the device including a component having one or more surfaces which come into contact with the medicament during storage or use of the device, in which said surfaces have a plasma deposited coating which has an oxygen content of less than 2 At % as measured by XPS.

Whilst the invention has been described above, it extends to any inventive combination as set out in the following description, drawings or claims.

Embodiments of methods and dispenser devices in accordance with the invention will now be described with reference to the accompanying drawings, in which.

Figure 1:
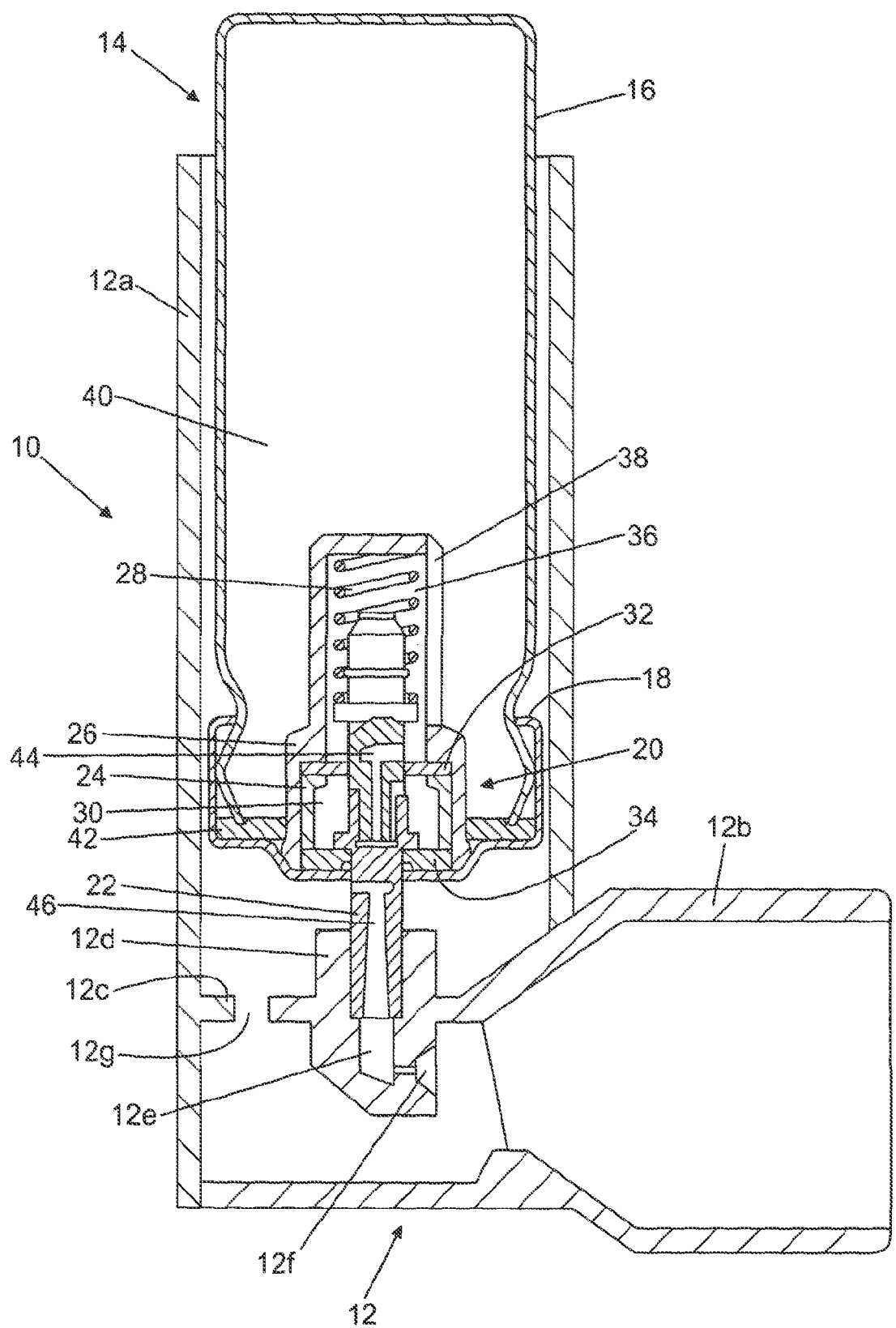
FIG. 1 is a cross sectional view of a pressurised dispenser device.

FIG. 1 depicts a pressurised dispenser device 10, which comprises a housing 12 which receives a pressurised medicament containing arrangement 14. The housing 12 comprises an open ended cylindrical portion 12a in which the pressurised medicament containing arrangement 14 is disposed, and an open ended passage 12b which serves as a mouthpiece. The housing 12 further comprises an inner wall 12c which supports a socket 12d having a passageway 12e which receives the valve stem of the pressured medicament container arrangement. The passageway 12e communicates with an opening 12f which in turn is in communication with the exit passage defined by the open ended passage 12b. The inner wall 12c has a number of apertures 12g formed therein which permits air to flow from the upper area of the housing 12 into the open ended passage 12b.

The structure and operation of the pressurised medicament container arrangement 14 will now be described in more detail. The arrangement 14 comprises a can body 16 on which is crimped a ferrule 18. Mounted on the ferrule 18 is a metering valve system, shown generally at 20. The metering valve system 20 comprises a valve stem 22, a portion of which is disposed in a valve member 24. The valve stem 22 and valve member 24 are both located in a valve housing 26, and the valve stem 22 is axially reciprocable therein against the action of a spring 28 which biases the valve stem 22 into a closed position as shown in FIG. 1.

The metering valve system 20 further comprises a metering chamber 30 which is defined by the valve member 24 and a portion of the valve stem 22 together with inner and outer seals 32, 34. The inner seal 32 acts to seal the valve member 24 against the valve housing 26, and separates the metering chamber 30 from the interior 36 of the valve housing 26. The outer seal 34 acts to seal the valve member 24 and valve housing 26 against the ferrule 18, and also seals the metering chamber 30 from the outside of the pressurised medicament container arrangement 14.

Further sealing is provided by a can body seal 42 which acts to seal the can body 16 against the ferrule 18 upon crimping of same. The valve housing 26 has a plurality of slots 38 which enable the interior 36 of the valve housing 26 to communicate with the interior 40 of the can body 16. The valve stem 22 has two channels 44, 46. Each channel, 44, 46 comprises a longitudinal passageway and a transverse passageway. The transverse passageway of the valve stem channel 44 is disposed so that, when the pressurised medicament container arrangement 14 is in its closed position as shown in FIG. 1, the metering chamber 30 is in communication with the interior 36 of the valve housing 26 and thus is also in communication with the interior 40 of the can body 16. As explained in more detail below, the volume of the metering chamber 30 corresponds to the volume of medicament containing fluid administered in a single dose. In the closed position shown in FIG. 1, the dose is wholly contained in the metering chamber 30 and cannot escape to the outside of the pressurised medicament container arrangement 14 owing to the action of the outer seal 34.

To release a dose of medicament containing fluid, the valve stem 22 is pushed against the biasing action of the spring 28 into the interior 36 of the valve housing 26 to an extent that the valve stem channel 44 no longer communicates with the metering chamber 30. The valve stem 22 is designed so that, in this dispensing position, the valve stem channel 46 of the valve stem 22 communicates with the metering chamber 30, thereby allowing the dose of medicament containing fluid in the metering chamber 30 to be dispensed through the valve stem 22. The dose then passes through the passageway 12e, opening 12f and open ended passage 12b to exit the device.

When the valve stem 22 is subsequently released, the biasing action of the spring 28 causes the valve stem 22 to move back towards the position shown in FIG. 1. Thus, the valve stem channel 46 assumes a position whereby the metering chamber 30 is sealed against the outside, and the valve stem channel 44 assumes a position whereby the interior 36 of the valve housing 26 is in communication with the metering chamber 30. Owing to the pressure differential between the relatively high pressure interior 40 of the can body 16 and the relatively low pressure of the metering chamber 30, the metering chamber 30 is refilled with another dose of the medicament containing fluid.

The pressurised dispenser device 10 shown in FIG. 1 is one example of such a device, and many other metering arrangements are known which differ to a greater or lesser degree in their precise mode of action. The present invention does not lay claim to the mode of action of the device shown in FIG. 1 or of any other pressurised dispenser device. Rather, the present invention provides devices and components for same having coatings thereon which inhibit losses of medicaments to internal surfaces of the device, and associated methods of production of such devices and components. The device shown in FIG. 1 is provided in order to assist the reader's appreciation of how the present invention might be applied. The skilled reader will appreciate that the present invention can be applied to other designs of pressurised dispenser devices than the one shown in FIG. 1, and indeed can be applied to different types of medicament dispenser devices than pressurised dispenser devices.

Figure 2:
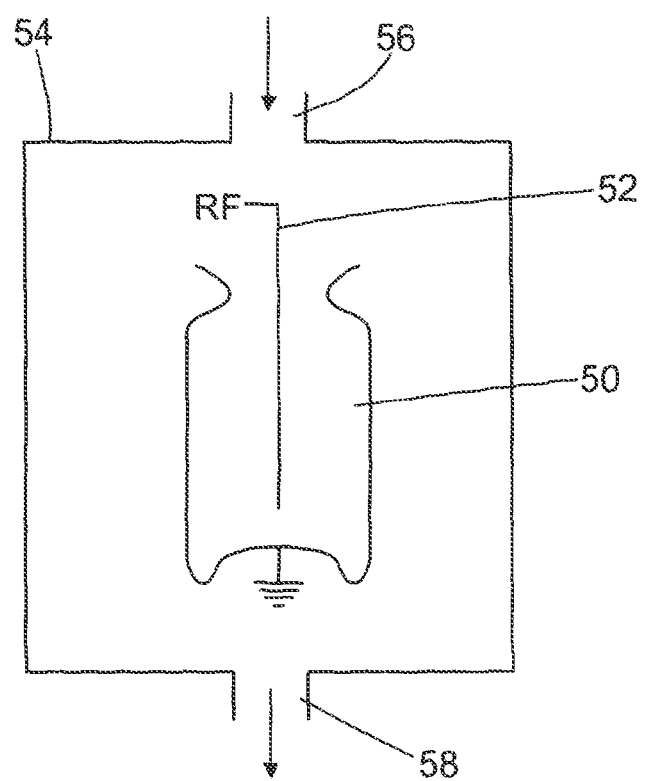
FIG. 2 shows an arrangement for coating a can body.

The present invention provides methods for depositing coatings which inhibit losses of the medicament to the internal surfaces of the pressurised dispensing device by providing various plasma polymerised coatings. FIG. 2 shows an arrangement in which a can body 50 is coated by plasma polymerisation. In the arrangement, the can body is maintained at earth, and an elongate RF electrode 52 extends into the interior of the can body 50 substantially along the longitudinal axis of the can body 50. The can body 50 is positioned in a plasma reactor 54 which has a gas/monomer feed inlet 56, and an outlet 58 for exhausting gases using a vacuum pump (not shown). The appropriate monomer or monomers are delivered into the can body 50 through the gas/monomer feed inlet 56 from an appropriate delivery source (not shown) which typically includes one or more mass flow controllers. A polymerised coating is deposited on the interior surfaces of the can body 50 by striking and maintaining a plasma whilst the monomer or monomers are flowed into the can body 50. Typically 13.56 MHz RF power is applied to the RF electrode 52, and the plasma is struck using techniques well known in the art. Other RF frequencies might be used, and it is anticipated that frequencies within the range of 4 kHz to 20 MHz might be utilised in either continuous power or pulsed mode. The plasma causes a thin coating of polymerised monomer to be deposited on the interior surfaces of the can body 50. It has been found that gas pressures in the range of $1 \times 10^{-2}$ to 10 mbar can be used. Power densities between 0.1 and 2 watts $cm^{-2}$ may be employed.

In a preferred embodiment, power is supplied to the RF electrode 52 to create a relatively intense plasma in order to provide an initial surface modification prior to deposition of the polymerised coating. The precursor gas may be a perfluorocarbon in order to produce a fluorinated surface having metal-fluorine moieties and a subsequent fluorocarbon polymerised coating, or may be a hydrocarbon precursor which is used to provide a modified surface having metal-carbide moieties and a subsequent hydrocarbon polymerised coating. Under representative process conditions, the oxygen content in the interior surface of the can body 50 is seen to drop from 40 to 44 At % to 8 to 10 At % as measured by XPS within two minutes of the commencement of processing. The aim is to drive the oxide level as low as possible. For the remainder of the process, the power supply is switched or maintained in DC bias mode, and the modified surface is coated with a plasma polymerised layer. With the configuration shown in FIG. 2, with the RF electrode 52 positioned in the earthed can body 50, the effective electrical resistance of the can increases as the can gets progressively coated. As a result, the normal electron path to the earthed can is reduced as the coating thickness increases. Forward power operation is typically used in prior art plasma polymerisation processes for coating components, such as can bodies, for medicament dispenser devices. However, under normal forward power operation, electron emission from the power supply will be reduced as the processing proceeds, self DC bias will be reduced, and plasma intensity will drop, resulting in a weak porous coating. In contrast, by operating a DC bias control, the DC bias is fixed, and a constant electron emission is maintained which in turn maintains a constant plasma density. This provides a constant deposition rate, and a high quality, uniform coating, both in terms of the lateral extent of the coating, and in terms of the depth coating. This steady rate of coating can be maintained until a desired thickness is obtained. Typically the desired thickness in the range of 15 to 200 nm, but the invention is not limited in this regard. A further advantage of DC bias control of the plasma polymerisation of a coating is encountered at the end of the process. It is typical in the prior art for coated components to be stored for between one and seven days so that reactive unsaturated surface sites on the coating are allowed to saturate. In the process described in relation to FIG. 2, the power supply and DC bias mode can be simply switched off, and the supply of the gaseous monomer is permitted to flow for a period thereafter, which is typically in the range of 5 seconds to 10 minutes, with a preferred range of 30 seconds to 1 minute. The intensity of the plasma drops off gradually as electrons in the capacitive reservoir are used up, allowing the surface to be flushed with a plasma containing relatively fewer and some larger ionised species, until the surface is flushed with "neat," unionised monomer. The effect is to "cap off" the coating with unreactive polymer and monomer which enables the coated component to be retrieved from the plasma reactor 54 without a subsequent rest period to unsaturation being required.

The configuration shown in FIG. 2 wherein the component to be treated is earthed and a separate RF electrode is used, is a preferred configuration for plasma polymerising a polymer coating. The configuration is also suitable for the earlier surface modification step. The advantage of using the same configuration for both the surface modification step and the subsequent plasma polymerisation step is that the two steps can be performed as part of one continuous operation. It is particularly advantageous as gas can be used both as the precursor to the surface modification step, and also as a monomer gas for the plasma coating step. When the surface of the component is converted to metal-fluoride moieties, the precursor can be $CF_4$, $C_2F_6$, $C_3F_8$, $C_4F_8$, HFA134a and HFA227. Where it is intended that modification of the components surface produces a metal carbide layer, it is preferred that the precursor/monomer is methane or ethane, but hydrocarbons from the range $CH_4$ to $C_6H_{14}$ can be utilised.

The component treated by the present invention may be subjected to a pre-cleaning step prior to the polymer deposition step (the cleaning step is also prior to the surface modification step when a surface modification step is utilised). It is common in the prior art to use a pre-cleaning step which utilises oxygen. The present inventors have realised that the use of oxygen in the pre-cleaning step, or indeed elsewhere in the processing of the component, is highly disadvantageous. The present inventors have found that the presence of oxygen is detrimental to the build up of deposited coatings and to their adhesion. Oxygen absorbed into e.g. the walls of the plasma reactor and other parts can leach out to dissociate the coating and/or the monomer, which is deleterious to the polymer and increases processing time. Any pre-cleaning step should therefore exclude oxygen. A particularly useful pre-cleaning step uses an argon plasma to clean the component prior to the surface modification step.

The embodiment shown in FIG. 2 is a can treatment process in which the can acts as an earth electrode. This has been found to provide particularly good results. Other coating configurations are possible. For example, in other configurations, the can may act as the RF electrode. However, with components such as cans, which have a substantially enclosed space, this configuration can be disadvantageous because a "hollow cathode effect" can occur in which a highly intense plasma is produced. This plasma can be of such intensity that any polymerised coating is removed by the plasma at a rate which is comparable to the deposition rate. It is common in the prior art to use another configuration in which the can is at a floating potential between two electrodes. However, the present inventors have realised that this is highly disadvantageous when the component is metallic, because surface charge cannot be held and instead dissipates. As a result, there is minimised attraction of ionic coating species, and it is found that weakly bound, porous cans are produced with decreased deposition rates.

Aluminium can bodies coated by plasma polymerising the range of hydrocarbons and perflurocarbons discussed have shown contact angles (using 1 µl water droplets) of in the range of 105 to 128°. XPS spectra of the finished coating shows that the species present consist mainly of bonds in a highly dense matrix, with less than 2.0 At % oxygen as C—O bonds and other oxygen functionalities. No aluminium is exposed.

The invention claimed is:

1. A method of treating a component of a medicament dispenser device, the component having one or more surfaces which come into contact with the medicament during storage or use of the device, the method including the steps of:
   providing said component; and
   coating at least one of said surfaces by plasma deposition thereby to inhibit surface deposition or degradation of the medicament, wherein at least part of the plasma deposition is performed under DC bias control;
   wherein the step of plasma deposition is initially performed without DC bias control, using forward power control, with DC bias control being commenced a period of time after plasma deposition begins.

2. The method according to claim 1 in which the plasma deposition comprises plasma polymerising at least one monomer.

3. The method according to claim 2 in which at least one monomer is one or more of a hydrocarbon, fluorocarbon, silane or siloxane.

4. The method according to claim 3 in which the monomer is a per-fluorocarbon.

5. The method according to claim 3 in which the monomer is ethane or $C_4F_8$.

6. The method according to claim 1 in which an inorganic coating is plasma deposited.

7. The method according to claim 1 in which DC bias control is performed using a DC bias voltage in the range of 50 to 800 volts.

8. The method according to claim 1 in which the component is earthed during the step of plasma deposition.

9. The method according to claim 8 in which the component is a can body, and during the step of plasma deposition an RF potential is applied to an electrode which is positioned within the can body.

10. The method according to claim 1 in which the step of plasma deposition is performed in a substantial absence of oxygen.

11. The method according to claim 10 in which the coating produced by the plasma deposition has an oxygen content of less than 10 At %.

12. A method of treating a component of a medicament dispenser device, the component having one or more surfaces which come into contact with the medicament during storage or use of the device, the method including the steps of:
   providing said component; and
   coating at least one of said surfaces by plasma deposition thereby to inhibit surface deposition or degradation of the medicament, wherein at least part of the plasma deposition is performed under DC bias control;
   wherein the plasma deposition comprises plasma polymerising at least one monomer and where power is supplied to the plasma during the step of plasma polymerising the monomer, and where this step is completed by turning off the power supplied to the plasma whilst maintaining a supply of the monomer so that the plasma diminishes by using up a capacitive reservoir of electrons thereby providing surface quenching of the coating.

13. The method according to claim 12 in which DC bias control is performed using a DC bias voltage in the range of 50 to 800 volts.

14. The method according to claim 12 in which the component is earthed during the step of plasma deposition.

15. The method according to claim 14 in which the component is a can body, and during the step of plasma deposition an RF potential is applied to an electrode which is positioned within the can body.

16. The method according to claim 12 in which the step of plasma deposition is performed in a substantial absence of oxygen.

17. The method according to claim 16 in which the coating produced by the plasma deposition has an oxygen content of less than 10 At %.

18. The method according to claim 12 in which at least one monomer is one or more of a hydrocarbon, fluorocarbon, silane or siloxane.

19. The method according to claim 18 in which the monomer is a per-fluorocarbon.

20. The method according to claim 18 in which the monomer is ethane or $C_4F_8$.

* * * * *